United States Patent [19]

Peers-Trevarton

[11] Patent Number: 4,458,695
[45] Date of Patent: Jul. 10, 1984

[54] MULTIPOLAR ELECTRODE ASSEMBLY FOR PACING LEAD

[75] Inventor: Charles A. Peers-Trevarton, Coral Springs, Fla.

[73] Assignee: Cordis Corporation, Miami, Fla.

[21] Appl. No.: 399,061

[22] Filed: Jul. 16, 1982

[51] Int. Cl.³ .............................................. A61N 1/04
[52] U.S. Cl. ............................ 128/786; 128/419 P
[58] Field of Search ............................... 128/784-786, 128/419 P, 642

[56] References Cited

U.S. PATENT DOCUMENTS

| 3,568,660 | 3/1971 | Crites et al. | 128/786 |
|---|---|---|---|
| 3,664,347 | 5/1972 | Harmjanz | 128/404 |
| 3,769,984 | 11/1973 | Muench | 128/786 |
| 3,804,098 | 4/1974 | Friedman | 128/786 |
| 3,825,015 | 7/1974 | Berkovits | 128/786 |
| 3,942,536 | 3/1976 | Mirowski et al. | 128/419 |
| 3,995,623 | 12/1976 | Blake et al. | 128/2.06 E |
| 4,073,287 | 2/1978 | Bradley et al. | 128/2 R |
| 4,402,328 | 9/1983 | Doring | 128/785 |

FOREIGN PATENT DOCUMENTS

| 0007157 | 1/1980 | European Pat. Off. | |
| 2494118 | 5/1982 | France | 128/419 P |
| WO80/02231 | 10/1980 | PCT Int'l Appl. | 128/786 |

Primary Examiner—Lee S. Cohen
Attorney, Agent, or Firm—Henry W. Collins; Thomas R. Vigil

[57] ABSTRACT

A cardiac lead having ring electrodes positioned at predetermined locations along the length of the lead either for stimulating the heart at various selected locations. The cardiac lead includes an insulative tubing having a plurality of apertures positioned at the distal end of the lead at selected locations along the length of the tubing. A plurality of coiled conductors are positioned within the tubing and each extend through a respective one of the apertures. The insulation is removed from the end of the conductor for that portion of the conductor extending outside of the insulative tubing, and this uninsulated portion of the conductor is coiled about the peripheral surface of the insulative tubing. A plurality of ring electrodes are each positioned to cover a respective one of the coils of uninsulated conductor.

4 Claims, 3 Drawing Figures

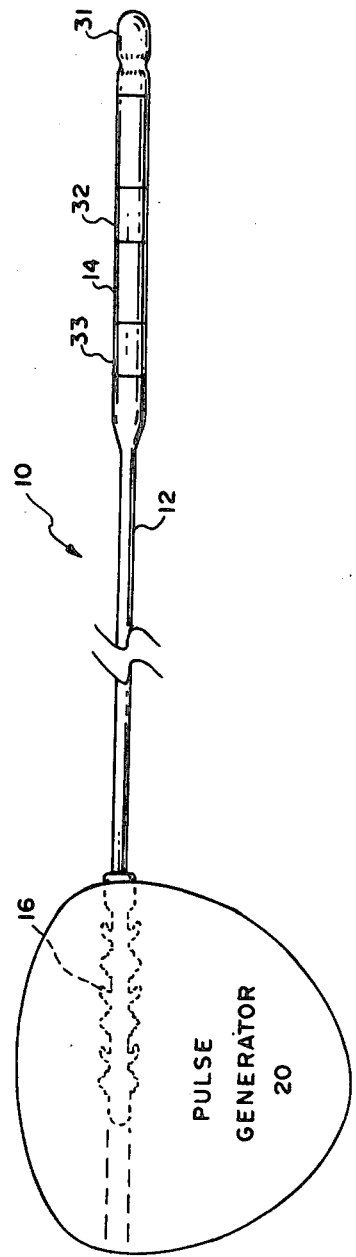
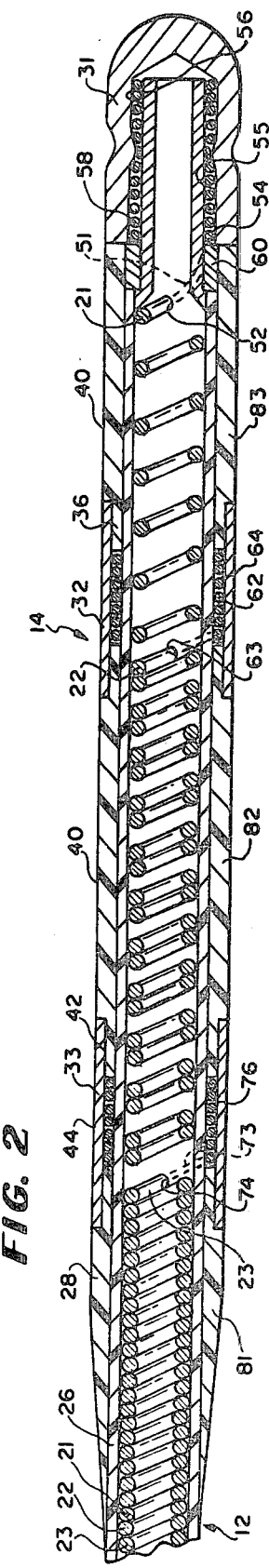
FIG. 1
FIG. 2

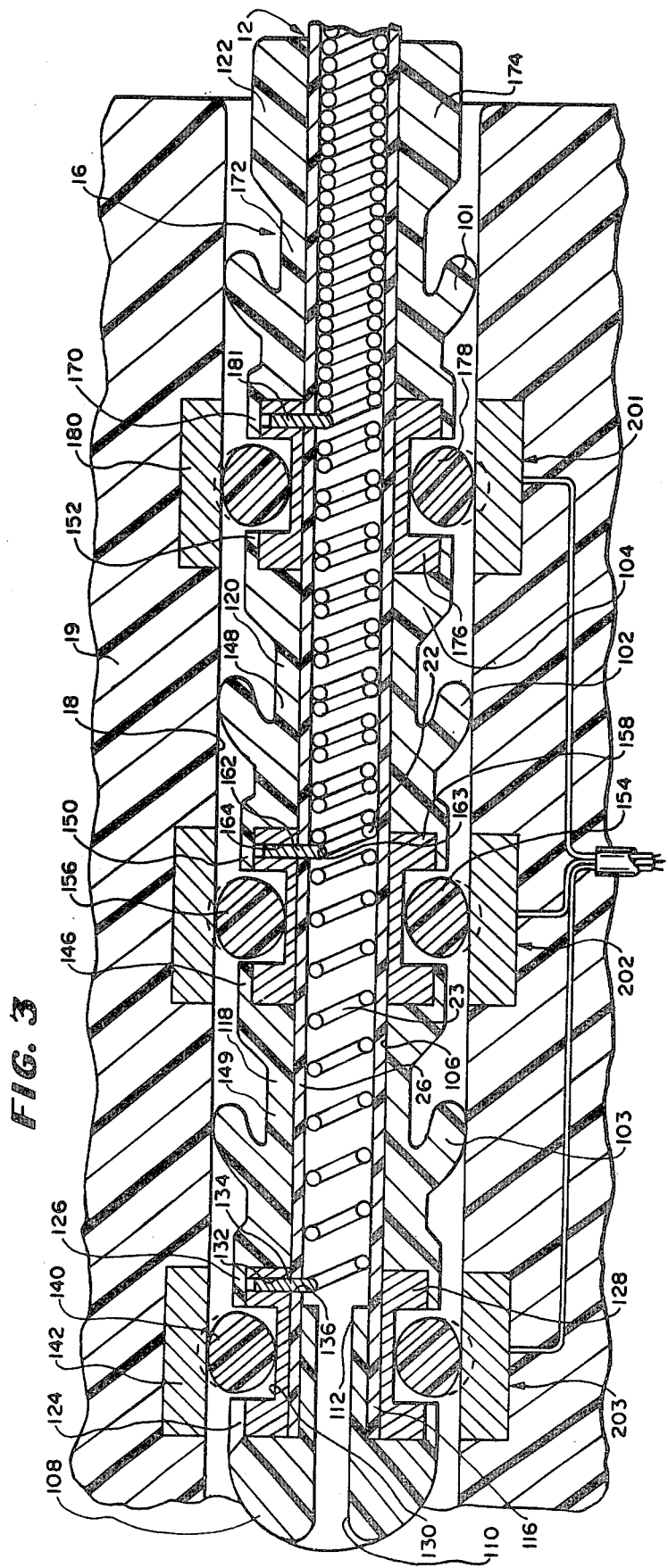

MULTIPOLAR ELECTRODE ASSEMBLY FOR PACING LEAD

BACKGROUND OF THE INVENTION

1. Field of the Invention

The present invention relates to a multipolar electrode assembly for use in pacing leads.

2. Description of the Prior Art

Multiple electrode cardiac pacing leads are well known and have been utilized for pacing both the atrial and ventricular chambers of the heart.

Cardiac stimulation requires a reliable means for connecting electrical signals from a pulse generator, or pacer, to a pre-selected region on the wall of the heart. For example, a certain type of cardiac pacing lead is connected to a pacer, extends into the heart, and is placed in contact with the inside wall of the right ventricle. This lead normally takes the form of a long, generally straight, flexible, insulated conductor having one end electrically connected to the pacer and the other end connected to an electrode. The electrode is placed in contact with the wall of the heart.

On the other hand, pacing leads which are used for stimulation of the atrium are generally formed in a J-shaped configuration so that when the lead is inserted through a blood vessel and into the heart, the lead may be positioned to curve up into the atrial cavity.

The present invention takes the form of a single, very flexible, multiple electrode pacing lead which may be positioned within the heart so that one or more of the electrodes may be utilized to apply stimulating pulses to the atrial or ventricular chamber.

Also as will be described in greater detail hereinafter, the multipolar electrode assembly at the distal end of the pacing lead of the present invention is constructed in such a way as to facilitate solid electrical contact between the ends of each wire conductor in the multiconductor lead and individual electrodes of the electrode assembly and in such a way as to take up a minimum of space thereby to provide a very compact small diameter electrode assembly.

SUMMARY OF THE INVENTION

The body implantable lead of the present invention includes an elongated, flexible, insulative tubing which has multiple pairs of closely spaced apertures extending through the wall at the distal end of the tubing at predetermined positions along the length of the tubing. Positioned within the insulative tubing are a plurality of coiled flexible electrical conductors. Each of the electrical conductors has an insulative coating which surrounds conductive wire over the entire length of the conductor except for proximal and distal terminal portions. The proximal terminal portion of each of the electrical conductors extends through one of the apertures and is coiled around the circumference of the insulative tubing. A ring-shaped conductor is positioned about the outer circumference of each of the coiled terminal portions of the electrical conductors to provide multiple pacing or sensing electrodes.

BRIEF DESCRIPTION OF THE DRAWINGS

FIG. 1 is a side view of a pulse generator and pacing lead assembly which are constructed in accordance with the teachings of the present invention.

FIG. 2 is an enlarged sectional view of a multipolar electrode tip assembly which is mounted at the distal end of the pacing lead assembly shown in FIG. 1; and, FIG. 3 is an enlarged sectional view of the multipolar insert connector at the proximal end of the pacing lead assembly shown in FIG. 1 received in a socket in a body portion of the pulse generator shown in FIG. 1.

DESCRIPTION OF THE PREFERRED EMBODIMENTS

Referring now to FIG. 1 there is illustrated therein a pulse generator and pacing lead assembly 10 which includes a multiconductor pacing lead 12 having at its distal end a multipolar electrode assembly 14 and a multipolar insert connector 16 at the proximal end thereof which is received within a socket 18 (FIG. 3) formed in a body portion 19 (FIG. 3) in a pulse generator 20.

Referring now to FIG. 2 there is illustrated therein a cross section of the multiconductor pacing lead 12 and of the multipolar electrode assembly 14. As shown, the multiconductor pacing lead 12 includes three conductors or wires 21, 22 and 23 which are wound in a single coil.

The coiled conductors 21, 22 and 23 are surrounded by an insulating sheath 26 which can be made of silicone, polyurethane, or other insulating material, but preferably is formed of PARYLENE "C" manufactured by Union Carbide Corporation.

The distal end of the pacing lead 12 extends within an electrode body 28 made of an insulating material and which forms part of the multipolar electrode assembly 14. Mounted at the distal end of the body 28 is a first electrode 31 which can be referred to as a tip electrode 31. Then, spaced from the tip electrode 31 is a second sleeve electrode 32 and a third sleeve electrode 33 is spaced from the second sleeve electrode 32. The sleeve electrode 32 is received in an annular slot 36 formed in the body 28 so that outer facing surface of the sleeve electrode 32 is flush with outer cylindrical surface 40 of the insulating body 28. Likewise, the second sleeve electrode 33 is an annular slot 42 in the insulating body 28 so that outer surface 44 thereof is flush with the cylindrical surface 40 of the insulating body 28.

Although not illustrated in FIG. 2, it is to be understood that each of the conductors or wires 21-23 has an insulating coating thereon so that it is insulated from the adjacent conductor.

As shown in FIG. 2, the first conductor 21 extends all the way to the first tip electrode 31 and an end portion 51 of the first conductor 21 extends through an opening 52 in the sheath 26. This end portion 51 is stripped of insulation and extends from the opening 52 in the sheath 26 through a slot (not shown) in the sheath 26 to an annular cavity 54 defined between an inner cylindrical surface 55 formed within the electrode 31 and outer surface 56 of a plug 58 which extends from the inner end of the sheath 26 around a ring 60 and into the cylindrical cavity 55. The electrode 31 is crimped at several points to retain the first conductor 21 between the outer surface 56 of the plug 58 and the inner cylindrical surface 55 of electrode 31 thereby to ensure a good electrical connection therewith.

In a similar manner, an end portion 62 of the second conductor or wire 22 is stripped of insulation so as to be a bare wire and extends through an opening 63 in the sheath 26 through a passageway in the sheath 26 to an annular passageway 64 where the bare conductor end portion 62 is coiled. The annular passageway 64 is defined between a thin layer (not shown) of electrode body 28 or the outer surface of the sheath 26 and the inner surface of the sleeve electrode 32. The width or thickness of the annular passageway 64 is such that the bare wire end portion 62 is urged against the inner surface of the sleeve electrode 32 thereby to ensure a good electrical contact therewith.

Further, and in like manner, the third conductor 23 has a bare end portion 73 which extends through an opening 74 in the sheath 26 and through a slot in the sheath 26 to an annular passageway 76 between a thin layer of the electrode body 28 or the outer surface of the sheath 26 and the inner surface of the third sleeve electrode 33. Also, the dimension or width of the annular passageway 76 is such that the bare conductor end portion 73 wound in a coil in the annular passageway 76 is urged against the inner surface of the sleeve electrode 33.

It will be appreciated from the foregoing description that the insulating body 28 which surrounds the distal end of the pacing lead 12 has been defined as one piece construction but is shown in FIG. 2 as being of three piece construction, namely of three elements 81, 82 and 83.

The multipolar electrode assembly 14, and in this particular instance, a three polar assembly 14, enables a physician to select any one of the three electrode 31, 32 or 33 for pacing the endocardium and for using any one of the electrodes 31, 32 and 33 for relaying information about selected tissue back to the pulse generator 20.

In FIG. 3 is illustrated the position of the insert connector 16 at the proximal end of the multiconductor pacing lead 12 received in the socket 18 in the body portion 19 of the pulse generator 20. As shown, the sidewall of the socket 18 is adapted to receive resilient flanges 101, 102 and 103 which extend from and are integral with an insulating body portion 104 of the insert connector 16. As shown in FIG. 3, when the insert connector 16 is inserted into the socket 18, the flanges 101, 102 and 103 will be flexed as shown for sealing the insert connector 16. Typically, the insulator body 104 and the flanges 101, 102 and 103 extending therefrom are made from an elastomeric insulating material such as silicone. The sealing arrangement shown in FIG. 3 is of the type shown in U.S. Pat. No. 4,259,962.

As shown in FIG. 3, the insulator body 104 has a central passageway 106 therein which is sized to receive the proximal end of the multiconductor pacing lead 12. The end 108 of the insulator body 104 of the insert connector 16 has a central passageway 110 therethrough which extends into the insulator body 104 and through a cylindrical protrusion 112 about which the proximal end 116 of the sheath 26 is received. This passageway 110 permits a stylet to be inserted through the passageway 110 and the insulator body 104 into the coiled conductors 21, 22 and 23 within the sheath 26 of the multiconductor pacing lead 12.

Although the insulator body 104 has been described above as being of unitary construction, it is preferably, and as shown in FIG. 3, made of insulating body segments which include the end segment 108, two identical intermediate segments 118 and 120 and an outer end segment 122. The end segment 108 has an outer annular flange 124 extending inwardly and axially of the insert connector 16 and is spaced radially outwardly from the cylindrical protrusion 112.

The intermediate segment 118 has a similar annular flange 126 which extends toward the annular flange 124 so as to define an annular space, open in the middle, between the outer surface of the sheath 26 and the annular flanges 124 and 126. Received within this annular space is a spool-shaped metal band or ring 128 which has an annular slot 130 therein. The spool-shaped metal band 128 has a radial slot 132 therein which receives the bare end 134 of the conductor 23 which bare end 134 extends from the insulated conductor 23 through an opening 136 in the sheath 26.

Received within the slot 130 in the spool-shaped metal band 128 is a resilient ring 140 of conductive material which is adapted to electrically contact the slot 130 on its inwardly facing side and to electrically contact a metal ring 142 embedded in the body 19 and having an inwardly facing surface flush with the surface of the socket 18.

The conductive ring 140 is preferably made of a conductive resilient material such as silicon rubber. Also, as shown in FIG. 3, the ring 140 has a diameter which is greater than the space between the outer surface of the spool-shaped metal band 128 and the metal ring 142 embedded in the body 19 and having an inner surface flush with the surface of the socket 18 so that the ring 140 will be squeezed when the insert connector 16 is inserted into the socket 18. This is brought out in FIG. 3 by the showing of the normal unsqueezed position of the ring in phantom in FIG. 3.

It is to be understood that the conductive ring 140 can also be made of other materials. For example, it could be a so-called garter spring which is a coiled spring in which two ends are brought together and welded so as to form a toroid envelope which can be squeezed when the insert connector 16 is inserted into the socket 18.

Another type of conductive ring would be a ring made of woven metal. In this respect, a flat sheet of woven metal could be rolled into a roll and then the roll formed into a toroid with the ends welded together, thereby to form a resilient ring 140. As is apparent, there are numerous other conductive materials and configurations thereof which could be utilized to form the conductive ring 140.

The insulator segment 118 in addition to having the radially extending annular flange 103 and the axially extending annular flange 126 has a reduced-in-diameter portion 149 for faciliating flexing of the flange 103 when the insert connector 16 is inserted into the socket 18. Further, the segment 118 has another axially extending annular flange 146 as shown.

The insulator segment 120 is identical to the insulator segment 118 and in addition to having a radially extending flange 102, it has a reduced-in-diameter portion 148 and annular flanges 150 and 152. The insulator segment 120 is positioned on the sheath 26 such that the annular flanges 150 and 152 form with the outer surface of the sheath 26 and annular space, open in the middle, for receiving a conductive resilient ring 154 which makes contact with a metal ring 156 embedded in the side wall of the socket 18 in the body portion 19 and the exposed surface of a spool-shaped metal band 158 received in the annular space. A bare end 162 of conductor 22 extends through an opening 163 in the sheath 26 and is received in a slot 164 in the spool-shaped metal band 158 for making electrical contact therewith. In this way as in the previous electrical connection described above, electrical contact is effected between the end 162 of the conductor 22 through the metal band 158 and resilient conductive ring 154 to metal ring 156.

The insulator segment 122 is similar in construction to insulator segments 118 and 120 by having an axially extending annular flange 170 at one end thereof, the radially extending flange 101 and a reduced-in-diameter section 172. The outer end of segment 122 is a solid body 174, as shown, which is received about the multiconductor pacing lead 12.

The opposed ends of the insulator segments 120 and 122 form an annular space for receiving a spool-shaped metal band 176 which has a conductive ring 178 extending thereabout and adapted to make electrical contact with a metal ring 180 embedded in the side wall of the socket 18. Also, a bare end 181 of conductor 21 extends through the sheath 26 where it is rigidly fixed into a slot in the spool-shaped metal band 176 to ensure a good electrical contact therewith.

It will be understood that the radially extending flanges 101, 102 and 103 can be sized and configured to sealingly fit against the side wall of the socket 18.

With the construction of the insert connector 16 and the socket 18 as described above, three electrical connector assemblies, 201, 202 and 203 are created for facilitating good electrical connection between the ends 134, 162 and 181 of the conductor 23, 22 and 21 to the pulse generator circuitry (not shown) within the pulse generator 20.

From the foregoing description it will be apparent that the pacing lead assembly for the present invention made according to the method of the present invention has a number of advantages, some of which have been described above and others of which are inherent in the invention. Also it will be apparent to those skilled in the art that modifications can be made to the pacing lead of the present invention without departing from the teachings of the present invention. Accordingly, the scope of the invention is only to be limited as necessitated by the accompanying claims.

I claim:

1. A pacing lead assembly comprising a multiconductor pacing lead having a distal end and a proximal end and including a plurality of individually insulated wire conductors within a sheath of insulating material, a multipolar electrode assembly mounted at said distal end of said multiconductor pacing lead and including a tip electrode having a cylindrical cavity therein and at least one sleeve electrode, first insulating means for insulating and spacing said tip electrode from said at least one sleeve electrode at said distal end of said multiconductor pacing lead, said first insulating means comprising a first sleeve of insulating material around said sheath, each wire conductor having a bared end portion, cylindrical support means for said bared end portions, said bared end portion of each said wire conductor being wound around said cylindrical support means beneath and in electrical contact with an inwardly facing conductive surface of one of said electrodes to form an electrical connection between each wire conductor of said multiconductor pacing lead and one of said electrodes, said support means beneath an inwardly facing conductive surface of said cylindrical cavity in said tip electrode being defined by a tubular member extending from a distal end of said sheath into said cylindrical cavity with said bared wire conductor end portion of one of said wire conductors being coiled about said tubular member and in electrical contact with the sidewall surface of said cylindrical cavity in said tip electrode, and said sheath having at least one opening therethrough through which one of said bared wire conductor end portions extends and is coiled about said sheath, which defines said cylindrical support means for that bared wire conductor end portion, to place that bared wire conductor in electrical contact with the inner surface of said at least one sleeve electrode.

2. The pacing lead assembly of claim 1 further comprising a second sleeve electrode spaced rearwardly from said first named sleeve electrode and positioned about said sheath, second insulating means comprising a second sleeve of insulating material between said first named sleeve electrode and said second sleeve electrode, and third insulating means comprising a third sleeve of insulating material extending rearwardly from said second sleeve electrode and tapering or blending to the surface of said sheath, said second sleeve of insulating material serving to space and insulate said first sleeve electrode from said second sleeve electrode, said sheath having an opening therein receiving a bared wire conductor end portion of one of said conductor therethrough, and said bared wire conductor end portion being coiled about said sheath beneath said second sleeve electrode and in electrical contact with said second sleeve electrode.

3. The pacing lead assembly of claim 2 wherein the opposed ends of said first and second sleeves of insulating material have portions cut away to form an annular first slot, said first sleeve electrode being received in said first slot, the opposed ends of said first and second sleeves of insulating material being spaced from one another beneath said first sleeve electrode to provide a space for one of said coiled bared wire conductor end portions, and said outer surface of said first sleeve electrode being flush with the outer surface of said first and second sleeves of insulating material, and wherein said opposed ends of said second and third sleeves of insulating material have portions cut away to form an annular second slot, said second sleeve electrode being received in said second slot, said opposed ends of said first and second sleeves of insulating material being spaced from one another beneath said second sleeve electrode to provide a space for one of said coiled bared wire conductor end portions, and said outer surface of said second sleeve electrode being flush with the outer surface of said second and third sleeves of insulating material.

4. The pacing lead of claim 1 wherein said tip electrode has a crimp therearound to force a wall portion of said cylindrical cavity against said bared wire conductor end portion in said cavity.

* * * * *

UNITED STATES PATENT AND TRADEMARK OFFICE
CERTIFICATE OF CORRECTION

PATENT NO.   : 4,458,695
DATED        : July 10, 1984
INVENTOR(S)  : CHARLES A. PEERS-TREVARTON It is certified that error appears in the above-identified patent and that said Letters Patent is hereby corrected as shown below:

Column 5, line 30 "for" should have been -- of --.

Column 6, line 14, after "conductor" insert -- end portion --.

Signed and Sealed this

Twenty-third Day of April 1985

[SEAL]

Attest:

DONALD J. QUIGG

Attesting Officer

Acting Commissioner of Patents and Trademarks